United States Patent [19]

Lalezari

[11] Patent Number: 5,498,708
[45] Date of Patent: Mar. 12, 1996

[54] METHOD OF SYNTHESIZING POLYESTERS

[75] Inventor: Iraj Lalezari, Scarsdale, N.Y.

[73] Assignee: Montefiore Medical Center, Bronx, N.Y.

[21] Appl. No.: 381,208

[22] Filed: Jul. 18, 1989

[51] Int. Cl.$^6$ .............................. C07H 1/00; C07H 13/02; C07H 15/04
[52] U.S. Cl. .................. 536/115; 536/116; 536/119; 536/120; 536/124
[58] Field of Search ................................ 536/119, 115, 536/116, 120, 124; 426/601, 602, 603, 605, 658, 653

[56] References Cited

U.S. PATENT DOCUMENTS

| | | | |
|---|---|---|---|
| 2,831,854 | 4/1958 | Tucker et al. | 536/119 |
| 2,931,802 | 4/1960 | Touey et al. | 536/119 |
| 3,057,743 | 10/1962 | Touey et al. | 536/119 |
| 3,096,324 | 7/1963 | Goins et al. | 536/119 |
| 3,251,827 | 5/1966 | Schnell et al. | 536/119 |
| 4,732,767 | 5/1988 | Seiden et al. | 426/654 |
| 4,780,542 | 10/1988 | Lalezari | 548/261 |
| 4,806,632 | 2/1989 | McCoy et al. | 536/124 |
| 4,840,815 | 6/1989 | Meyer et al. | 536/4.1 |
| 4,987,237 | 1/1991 | Myers et al. | 536/117 |

*Primary Examiner*—Michael G. Wityshyn
*Assistant Examiner*—Everett White
*Attorney, Agent, or Firm*—Hedman, Gibson & Costigan

[57] ABSTRACT

A new process is disclosed for the preparation of esters of polyhydroxy compounds having three or more hydroxy compounds. The process is based on the reaction with an alkyl chloroformate to form a mixed anhydride which is contacted with a polyol.

15 Claims, No Drawings

METHOD OF SYNTHESIZING POLYESTERS

FIELD OF THE INVENTION

The field of this invention is esters of polyhydroxy compounds having three or more hydroxy groups. In particular, the invention comprises a process for the manufacture of such esters.

BACKGROUND OF THE INVENTION

Processes for the preparation of esters of polyols are known. The particular polyols that have been esterified include the non-reducing oligosaccharides and the polysaccharides. The prior art processes have included the direct esterification method; the reaction of the polyols with an acid anhydride; the reaction of the polyol with an acid halide; and a transesterification reaction using alkyl or aryl esters. The prior art processes have utilized some type of an organic solvent and have generally required extensive recovery operations to obtain a pure product. A mixed carboxylic-carbonic anhydride reaction for making amides and esters in an organic solvent is described in Nelson; J. Org. Chem. 28:1905 (1963).

The applicant has discovered a process for the preparation of esters of polyols which is based on the preparation of mixed carboxylic-carbonic anhydride in a aqueous system.

Therefore, it is a primary object of this invention to provide a process for the preparation of esters of polyols.

It is also an object of this invention to provide a process for the preparation of esters of polyols that is carried out in an aqueous system.

DETAILED DESCRIPTION OF THE INVENTION

The esters that may be prepared according to the process of the invention include those of the formula:

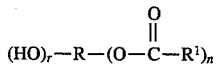

wherein R is the carbon residue of a polyol, $R^1$ is selected from straight or branched chain alkyl or hydroxy alkyl groups of from 3–30 carbon atoms; straight or branched chain alkenyl or hydroxy alkenyl of from 3–30 carbon atoms; alkaryl; aralkyl; aryl; cycloalkyl of from 5 to 7 carbons; and mixtures thereof; n is from 1 to the number of replaceable hydroxyl groups on the polyol; r is 0 or is equal to the number of unesterified OH groups; n+r are equal to the total number of replaceable OH groups in the polyol.

The term polyol is used to include all compounds having a carbon backbone and 3 or more hydroxy groups. Within this definition are included diols triols such as glycerine; 1,1,1-trimethylol ethane; 1,1,1-trimethylol propane; tris-hydroxy ethyl isocyanurate; tetrols such as erythritol and pentaerythriol; pentols such as adonitol; hexols such as sorbitol; mannitol and galactitol; cyclic hexols such as inositol; hexoses such as glucose; dextrose; fructose; xylose; pentoses such as ribose; reducing and non-reducing oligosacchrides including the disaccharides maltose; lactose; sucrose; cellobiose; trisaccharides such as raffinose; polysaccharides such as starches, e.g., amylose; and cellulose; heteropolysaccharides such as inulin and agar. Polyvinyl alcohol may also be esterified according to the process of the invention.

Preferred are oligosaccharides having 7–16 hydroxyl groups per molecule. U.S. Pat. No. 4,806,632; U.S. Pat. No. 2,831,854 and U.S. Pat. No. 3,251,827, describes a number of esters and oligosaccharides which may be prepared by the process of the present invention and therefore, are incorporated by reference. Other polyols are set forth in Noller, Textbook of Organic Chemistry pp. 276–299, which are incorporated by reference.

The term alkaryl is used herein to describe alkyl substituted aromatic groups wherein the alkyl group has from 1 to 6 carbons atoms and the aromatic group is phenyl or naphthyl; the term aralkyl is used to described groups wherein an aryl group such as phenyl or naphthyl is substituted onto an alkyl group of from 1 to 6 carbon atoms; the term aryl has been used to include phenyl and naphthyl; the term alkenyl is used to include hydrocarbon groups having one, two or three double bonds; the term arylene has been used to include phenylene and naphthylene; and the term alkylene has been used to include $-(CH_2)-_m$ groups wherein m is from 1 to 10. The terms aralkyl and alkaryl are used to include groups which include $-(CH_2)_m-$aryl; $-(CH_2)_m$-arylene $(CH_2)_m$; and aryl $(CH_2)_m$ arylene.

The various carbon atoms of $R^1$ also be substituted with halogens such as chloro or bromo. The acids which are used to form the esters may have from 2–30 carbon atoms, preferably from 8–22 carbon atoms. The acids include saturated and unsaturated acids such as propanoic, butanoic, pentanoic, lauric, myristic, palmitic, stearic, oleic, linoleic, linolenic, eleostearic acid, mixtures thereof and the like.

Natural sources of these acids may also be used after removal of the glycerol moiety from the naturally occurring material using conventional techniques. Examples of these materials include corn oil, soy oil, sunflower oil and the like. Other acids, and natural sources of these materials and polyols are described in Noller, Textbook of Organic Chemistry, 2nd Ed (1958) W. B. Saunders & Co. pp. 112, 138–142, which are incorporated herein by reference.

The process of the invention may be practiced by combining in a suitable reactor, the polyol and the acid in the presence of an amino compound, preferably a tri-alkyl amine such as tri-ethyl amine. The reaction is preferably carried out in a 100% aqueous reaction medium such as purified or distilled water. The amount of water may comprise from 0.1 to 20 liters of water per mole of acid. The insoluble or slightly soluble acids should be dispersed in a larger volume of water than is used for a soluble acid. A true solution is not required for the process of the invention. If desired, a non-reactive dispersing agent may be used in the reaction to assist in the dispersion of insoluble or slightly soluble acids. After the esters are formed, they may be separated directly from the reaction mixture using centrifugation, filtration or other conventional techniques. In the alternative, it may be expedient to extract the ester in a water immiscible organic solvent such as ether, petroleum ether, methylene chloride, and the like.

The extracted ester may be recovered or washed with water or any other suitable washing fluid.

It is preferred to utilized an alkyl chloroformate of the formula:

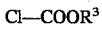

wherein $R^3$ is alkyl of from 1–10 carbon atoms or aryl such as phenyl. Ethyl chloroformate is the preferred compound. The chloroformate is first reacted with the acid or mixture of acids to form a mixed anhydride of the formula:

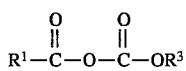

wherein $R^1$ and $R^3$ are the same as hereinabove defined. The mixed anhydride is then contacted with the polyol to form the ester. The fully esterified polyol will be obtained if about one mole of acid is used for each esterifiable hydroxyl group. If partial esters are to be prepared, the molar ratios may be adjusted to esterify less than all of the hydroxyl groups. Mixtures of esters are obtained, then may be separated using conventional techniques. Mixed esters may be prepared by using mixtures of acids or mixtures of polyols.

Most of the esters are known compounds. All of the esters may be used as components of cosmetic compositions for their emollient properties. Mixtures may also be used for this purpose. Generally, the esters may be added to petrolatum or synthetic cosmetic bases in amounts of from 1–50% by weight or more. The cosmetic bases are described in Remingtons Practice of Pharmacy, 13th Ed., which is incorporated by reference. Certain of the esters which have a sufficiently high viscosity may be used as lubricants or additives of lubricating compositions. Certain of the oligosaccharide esters, such as those derived from sucrose and acids of 12–22 carbon atom, preferably 14–20 carbon atoms, may be used as non-nutritive foodstuffs.

The invention also includes the method of preparing a foodstuff by contacting an edible base material with an ester of a reducing mono-, di-, tri- or tetrasaccharide and a fatty acid having 12–22 carbon atoms. The process is carried out by heating the components at a temperature and for a time which will cook the edible base material. In particular, the use of esters of maltose with a fatty acid of 12–22 carbons; in compositions with edible base materials is also included in the invention. The term edible base material is used to include nutritive materials such as sugar, flour and the like as well as cellulose and other forms of cellulose, e.g., microcrystalline cellulose. These materials are disclosed in U.S. Pat. No. 4,368,213; U.S. Pat. No. 4,461,782 and U.S. Pat. No. 4,732,767, which are incorporated by references.

The following examples are added to illustrate the process of the invention and are not intended to limit the scope of the invention.

EXAMPLE 1

A mixture of myristic acid 4,567 g. (0.02 mol); 40 ml water; 4 ml of triethyl amine; 4 ml of ethyl chloroformate in 40 g. of crushed ice was combined with sitrring in a beaker immersed in a 10% salt-crushed ice mixture. After about one-half hour of stirring, a mixture of 1,711 g. (0,005 mol); 10 ml of water and 50 g. of crushed ice was added and stirred one hour until the mixture reached room temperature. Gradually, an oil (semi-solid) appears. It could be separated from the water directly (e.g., centrifugation), but petroleum ether was used as a solvent to extract the product. The solvent was evaporated and the solid was washed with a saturated solution of potassium bicarbonate and dried over anhydrous magnesium sulfate. The yield was 5.62 g. (97.4% on the basis of 4 mol of fatty acids per one mol of sucrose).

EXAMPLE 2

A mixture of 4.0 g. of lauric acid (0.02 mol); 50 ml of water, 4 ml of ethyl chloroformate in 30 g. of crushed ice was combined with 0.9 g. of D(+) maltose $H_2O$ (0.0025 mol) in 1 ml of water and 30 g. of crushed ice according to the procedure of Example 1. The product was extracted with methylene chloride and 4.7 g. (100% of theoretical) of a semi-solid oily product was obtained.

EXAMPLE 3

A mixture of 5,689 g. (0.02 mol) of stearic acid; 60 ml of water; 4 ml of ethyl chloroformate; 4 ml of triethylamine; and 30 g. of crushed ice were combined in 1.711 g. (0.005 mol) of β-lactose in 10 ml of water and 50 g. of crushed ice using the general procedure of Example 1. The powdery white material which separates is filtered using suction and washed with saturated potassium bicarbonate solution. The product is dried for three days to constant weight at room temperature. The yield is 5.65 g. (80%).

EXAMPLE 4

A mixture of 1,564 g. (0.01 mol) of palmitic acid; 25 ml of water; 2 ml of triethyl amine; 2 ml of ethyl chloroformate and about 30 g. of crushed ice was combined with 0.375 g. (0.0025 mol) of D(−)arabinose; 5 ml water; 20 g. of crushed ice using the general procedure of Example 1. The reaction mixture was extracted with petroleum ether and worked up in accordance with the procedures of Example 1. The product was a low melting point wax and the yield was 100% of the theoretical.

EXAMPLE 5

A mixture of myristic acid 4.567 g. (0.02 mol); 40 ml of water; 4 ml of triethylamine; 40 g. of crushed ice is combined with D(−)ribose 0.75 g.; 10 ml of water and 30 g. of crushed ice in accordance with the procedure of Example 1. After extraction with ether and washing with potassium bicarbonate, 5.43 g. of product (100% yield) was obtained.

EXAMPLE 6

A mixture of 5.684 g. (0.02 mol); 60 ml of water; 4 ml of triethylamine; 4 ml of ethyl chloroformate; 30 g. of crushed ice is combined with 3,423 g. (0.01 mol) of sucrose; 15 ml of water; 30 g. of crushed ice. The reaction product was extracted with methylene chloride, washed with potassium bicarbonate and water to obtain 7.2 g. of product (80% yield).

EXAMPLE 7

A mixture of 2.825 g. (0.001 mol) of oleic acid; 2.844 g. of stearic acid (0.01 mol); 60 ml of water; 4 ml of ethyl chloroformate; 4 ml of triethylamine; 30 g. crushed ice was combined with 1.711 g. of sucrose (0,005 mol); 10 ml water and 30 g. of crushed ice according to the procedure of Example 1. The product was extracted with methylene chloride, washed with potassium bicarbonate solution and dried. The yield was 7.2 g. (95%).

EXAMPLE 8

A mixture of 5.128 g. of palmitic acid (0.02 mol); 4 ml triethylamine; 4 ml of ethylchloroformate; 30 g. of crushed ice was combined with 0.610 g. of meso-erythritol (0.005 mol); 10 ml of water and 20 g. of crushed ice according to the procedure of Example 1. A semi-solid oily material was extracted with dichloro-methane, washed with potassium bicarbonate solution and dried. A crystalline white waxy solid weighing 5.7 g. (100%) is obtained.

EXAMPLE 9

A mixture of 5.709 g. (0.025 mol) of myristic acid; 5 ml of triethylamine; 5 ml of ethyl chloroformate; 50 ml of water and 50 g. of crushed ice is combined with 0.760 g. (0.005 mol) of adonitol; 10 ml of water and 20 g. of crushed ice according to the procedure of Example 1. The product was extracted with methylene chloride, separated and washed according to the procedure of Example 1 to provide 100% of the theoretical yield.

EXAMPLE 10

A mixture of 5.709 g. of myristic acid (0.025 mol); 60 ml of water; 5 ml of triethylamine; 5 ml of ethyl chloroformate; 48 g. of crushed ice are combined with 0.9 g. of α-D-glucose (0.005 mol); 10 ml of water and 20 g. of crushed ice according to the procedure of Example 1. A white mass was obtained in 100% of the theoretical yield.

EXAMPLE 11

A mixture of 8.473 g. (0.03 mol) of oleic acid; 75 ml of water; 6 ml of triethyl amine; 6 ml of ethyl chloroformate; and 50 g. of crushed ice are combined with 1.711 (0.005 mol) of sucrose; 10 ml of water and 50 g. of crushed ice. The product is extracted with petroleum ether, washed with potassium bicarbonate solution and water to obtain 10 g. (100%) of a light yellow oil which is not cloudy at $-5°$ and has a very slight odor of oleic acid.

EXAMPLE 12

A mixture of 5.689 g. of stearic acid (0.02 mol); 6 ml of water; 4 ml of ethylchloroformate and 30 g. of crushed ice is combined with 6.846 g. (0.02 ml) of sucrose; 30 ml of water and 60 g. of crushed ice according to the procedure of Example 1. After extraction with methylene chloride; washing with potassium bicarbonate solution and water, 7.07 g. (58% yield) of a solid is obtained.

EXAMPLE 13

A mixture of 5.689 g. (0.02 mol) of stearic acid; about 60 ml of water; 4 ml of triethylamine; 4 ml of ethyl chloroformate and 40 g. of crushed ice is combined with 0.6 g. (0.00332 mol) of myo-inositol; 20 ml of water and 40 g. of crushed ice according to the procedure of Example 1. A white powder was obtained which was air dried to a weight of 6.55 g. in 24 hours m.p. $54°$–$55°$.

EXAMPLE 14

A mixture of lauric acid 2.0 g. (0.01 mol); 30 ml of water; 2 ml of triethylamine; 2 ml of ethyl chloroformate; 20 g. of crushed ice is combined with 0.3 g. (0.00166 mol) of myo-inositol; 10 ml of water and 20 g. of crushed ice in accordance with the procedure of Example 1. After extraction with petroleum ether and washing, a colorless fluid was obtained which weighed 2.28g. (100% of theoretical).

EXAMPLE 15

A mixture of stearic acid 8.53 g. (0.03 mol); 75 ml of water; 6 ml of triethylamine; 6 ml of ethylchlorofomate and 30 g. of crushed ice is combined with 0.911 g. (0.005 mol) of D-sorbitol; 10 ml of water and 50 g. of crushed ice according to the procedure of Example 1. After a butter like material separated, heat was applied ($80°$ C.) to melt the product and decompose residual ethylchloroformate. A yield of 9.05 g. is obtained.

I claim:

1. A process for the preparation of an ester which comprises contacting an acid with an alkyl chloroformate in an aqueous medium that is 100% water to form an anhydride and thereafter contacting said anhydride with a polyol to form said ester.

2. A process as defined in claim 1 wherein said ester is of the formula:

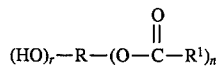

wherein R is the carbon residue of a polyol; $R^1$ is selected from straight or branched chain alkyl or hydroxy alkyl groups of from 3 to 30 carbon atoms; straight or branched chain alkenyl or hydroxy alkenyl of from 3 to 30 carbon atoms; alkaryl; aralkyl; aryl; cycloalkyl of from 5 to 7 carbons and mixtures thereof; n is from 1 to the total number of replaceable hydroxyl groups on the polyol; r is 0 or is equal to the total number of unesterified OH groups; n+r are equal to the total number of replaceable OH groups in the polyol.

3. A process as defined in claim 2 wherein the polyol is a reducing oligosaccharide.

4. A process as defined in claim 3 wherein the reducing oligosaccharide is a disaccharide selected from the group consisting of maltose, cellobiose and lactose.

5. A process as defined in claim 2 wherein the polyol is a non-reducing disaccharide.

6. A process as defined in claim 5 wherein the non-reducing disaccharide is selected from the group consisting of sucrose, trehalose and glucoxylose.

7. A process as defined in claim 6 wherein the acid has from 2–30 carbon atoms.

8. A process as defined in claim 5 wherein the non-reducing disaccharide is sucrose.

9. A process as defined in claim 7 wherein the acid has from 8–22 carbon atoms.

10. A process as defined in claim 9 wherein the acid has from 12 to 22 carbon atoms.

11. A process as defined in claim 10 wherein the polyol is sucrose and the acid has from 12 to 22 carbon atoms.

12. A process as defined in claim 10, wherein the acid is derived from an saponified oil.

13. A process for the preparation of an ester which comprises contacting an acid of the formula

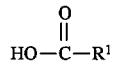

wherein $R^1$ is selected from straight or branched chain alkyl or hydroxy alkyl groups of from 3 to 30 carbon atoms; straight or branched chain alkenyl or hydroxy alkenyl of from 3 to 30 carbon atoms; alkaryl; aralkyl; aryl; cycloalkyl of from 5 to 7 carbons and mixtures thereof with a chloroformate of the formula

wherein $R^2$ is alkyl of 1 to 10 carbon atoms or aryl to form a mixed anhydride of the formula

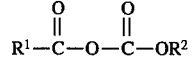

in an aqueous medium which is 100% water to form a reaction mixture and thereafter contacting said reaction mixture with a polyol of the formula R(OH)$_p$ wherein R is the carbon residue of a polyol, wherein p is a number of from 3 to 12.

14. A process for the preparation of an ester which comprises contacting an acid of the formula $$HO-\overset{O}{\underset{\|}{C}}-R^1$$

wherein R$_1$ is selected from straight or branched chain alkyl or hydroxy alkyl groups of from 3 to 30 carbon atoms; straight or branched chain alkenyl or hydroxy alkenyl of from 3 to 30 carbon atoms; alkaryl; aralkyl; aryl; cycloalkyl of from 5 to 7 carbons and mixtures thereof with a chloroformate of the formula Cl—COOR$_2$ wherein R$_2$ is alkyl of 1 to 10 carbon atoms or aryl to form a mixed anhydride of the formula $$R^1-\overset{O}{\underset{\|}{C}}-O-\overset{O}{\underset{\|}{C}}-OR^2$$

in an aqueous medium which is 100% water to form a reaction mixture and thereafter contacting said reaction mixture with sucrose.

15. A process as defined in claim 14, wherein the acid has from 8–22 carbon atoms.

* * * * *